United States Patent [19]

Schookin et al.

[11] Patent Number: 5,685,316

[45] Date of Patent: Nov. 11, 1997

[54] NON-INVASIVE MONITORING OF HEMODYNAMIC PARAMETERS USING IMPEDANCE CARDIOGRAPHY

[75] Inventors: Sergei I. Schookin; Viatcheslav G. Zubenko; Konstantin R. Beliaev; Aleksandr A. Morozov, all of Moscow, Russian Federation; Wen H. Yong, Singapore, Singapore

[73] Assignee: Rheo-Graphic PTE Ltd., Singapore, Singapore

[21] Appl. No.: 629,420

[22] Filed: Apr. 8, 1996

[51] Int. Cl.⁶ .................................................. A01B 5/0295
[52] U.S. Cl. ................................................................. 128/713
[58] Field of Search .................................. 128/734, 723, 128/693, 213, 211, 696

[56] References Cited

U.S. PATENT DOCUMENTS

| | | |
|---|---|---|
| 4,450,527 | 5/1984 | Sramek . |
| 4,458,694 | 7/1984 | Sollish et al. ........................ 128/734 |
| 4,807,638 | 2/1989 | Sramek . |
| 4,836,214 | 6/1989 | Sramek . |
| 4,854,327 | 8/1989 | Kunig . |
| 4,953,556 | 9/1990 | Evans . |
| 5,046,502 | 9/1991 | Kunig . |
| 5,261,411 | 11/1993 | Hughes ................................. 128/713 |
| 5,265,615 | 11/1993 | Frank et al. . |
| 5,309,917 | 5/1994 | Wang et al. . |
| 5,402,795 | 4/1995 | Reichl .................................... 128/698 |
| 5,406,955 | 4/1995 | Bledsoe et al. ........................ 128/711 |
| 5,423,326 | 6/1995 | Wang et al. . |
| 5,503,157 | 4/1996 | Sramek . |
| 5,505,209 | 4/1996 | Reining . |

OTHER PUBLICATIONS

Arinchin, V.I. et al. "Taking Into Account Electrical Resistance of Blood Will Increase Accuracy of Chest Tetrapolar Rheography Method", *Pediatric(SU Journal)*, 1987, N7, p. 59–62.

*Primary Examiner*—William E. Kamm
*Attorney, Agent, or Firm*—Trask, Britt & Rossa

[57] ABSTRACT

A method and apparatus for determination of heart rate, heart stroke volume, and cardiac output from thoracic bioimpedance signals. A unique bioimpedance electrode arrangement is employed, and the bioimpedance signals are corrected for gain-phase-frequency distortion through the use of sinusoidal test signals through the measuring or detection electrodes to identify distortions and correct for same during actual measurements. Time-derivative bioimpedance signals are employed, the power spectrum calculated, and a novel autoconvolution procedure used to emphasize the heart rate harmonic. Breath waves and other signals not indicative of the patient's cardiocycles are removed. Left ventricular ejection time is derived from the bioimpedance signals, and an improved version of Kubicek's equation is employed to derive heart stroke volume and thus cardiac output.

25 Claims, 6 Drawing Sheets

NON-INVASIVE MONITORING OF HEMODYNAMIC PARAMETERS USING IMPEDANCE CARDIOGRAPHY

BACKGROUND OF THE INVENTION

1. Field of the Invention

The present invention relates generally to cardiac monitoring and specifically to the determination of heart rate (HR), heart stroke volume (SV), and cardiac output (CO) according to thoracic bioimpedance signals.

2. State of the Art

Heart rate is the number of times the heart beats per minute. Heart stroke volume is the volume of blood pumped during each heart stroke. Cardiac output is the volume of blood pumped in one minute and is generally considered to be the most significant gauge of cardiac fitness. Physicians must frequently rely upon such cardiac parameters to diagnose heart disease, to assess a patient's overall health, to determine the most appropriate method of treatment, and to quickly discover sudden lapses in cardiac performance.

The currently existing methods for measuring cardiac output and other cardiac parameters may be divided into two categories: invasive and noninvasive. The invasive methods require that a medical practitioner insert a measuring device into the patient's body, such as a catheter in the throat, and present numerous disadvantages to both patient and physician. The patient must often endure substantial pain and discomfort and the physician must perform a relatively complicated procedure and occasionally expose himself or herself to the risk of contact with infectious blood. The noninvasive methods currently in use represent a major advancement, but still have significant shortcomings. Most take measurements using ultrasound, phonocardiography, or electrical bioimpedance in order to calculate cardiac parameters.

The methods which employ bioimpedance measurement involve placing a plurality of electrodes on a patient's skin (predominantly in the thoracic region), generating a high frequency, low amplitude electric current from certain of the electrodes into the patient's body, measuring the changes in the electrical impedance of the patient's tissue over time, and correlating the changes in electrical impedance with cardiac parameters.

Figure 1:
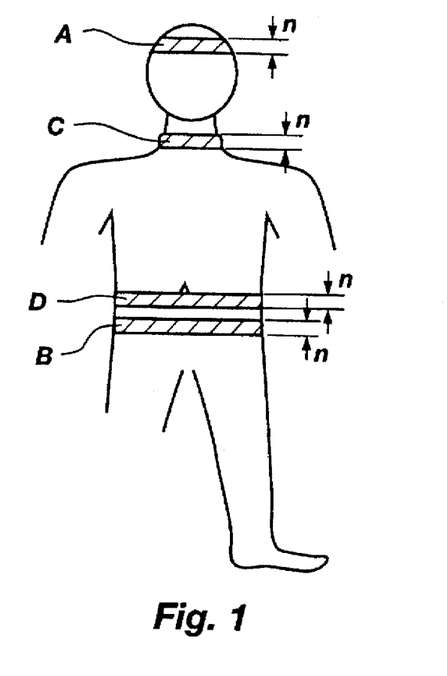
FIG. 1 is a schematic depiction of a band-type electrode arrangement on a patient.

The manner of arranging the electrodes on the patient's body plays an important part in the relative accuracy of the ultimate cardiac parameter measurements. Due to various anatomical factors, electrodes must be placed over certain areas of the body to achieve optimum correlation between measured changes in bioimpedance and cardiac parameters. Many of the electrode configurations currently in use fail to adequately take into account the paths followed by the lines of electrical potential through the thorax and thus create a distortion in the cardiac measurement. Moreover, a few electrode arrangements require the use of band electrodes (see FIG. 1) which wrap around a patient like a belt and further limit access to the patient, an especially undesirable condition during reanimation procedures. The movements associated with respiration also make band electrodes very inconvenient when placed on the neck and chest.

Perhaps the most significant problem with the presently existing bioimpedance methods is the imprecise mathematical derivation of cardiac parameters from bioimpedance measurements. The ventricular ejection time (VET) is a measurement of the time between the opening and closing of the aortic valves during the systolediastole cycle of the heartbeat and it must be calculated as an intermediate step in determining cardiac stroke volume. The prior art does not teach a method for determining ventricular ejection time with sufficient accuracy. Furthermore, the prior art fails to account for the fact that VET is not a single event. In reality, there is actually a left VET and a right VET. It has been shown that the time-derivative impedance signal is actually proportional to the peak aortic blood flow ejected by the left ventricle. The measurements of left VET and right VET for most patients are generally very close, but even slight differences between them can create errors in bioimpedance readings under the methods currently in use.

The conventional equation for deriving stroke volume from bioimpedance signals has become known as the Kubicek equation and is given as follows:

$$SV = R(L/Z_0)^2 (VET)(dZ/dt_{min}),$$

where SV is heart stroke volume, R is blood resistivity, L is the distance between the inner and outer voltage sensing electrodes, $Z_0$ is the mean thoracic impedance determined from the inner voltage sensing electrodes, VET is the combined left and right ventricular ejection time, and $dZ/dt$ is the maximum negative slope change of the time-differentiated impedance signal. Most bioimpedance cardiac monitoring systems use some form of the Kubicek equation. Without further refinement, however, the Kubicek equation frequently gives inaccurate measurements. This is due in part to the fact that both ventricles contribute to impedance changes, and so Kubicek's calculated ejection time (VET) cannot be associated with a particular, specifically the left, critical ventricle. Kubicek's SV calculation is often proportional to, but not equal to, the actual heart stroke volume and must therefore be multiplied by some correlating constant. In addition, the prior art does not disclose a method for adjusting R in accordance with the fluctuation of a patient's hematocrit (red blood cell count). The adjustment of R is especially important in patients undergoing blood infusion.

Many of the methods for bioimpedance cardiography require that the patient hold his or her breath during each measurement because respiration causes interference in the bioimpedance signal. Such methods are inconvenient for some patients and completely useless for other patients who are unconscious or otherwise unable to hold their breath. Some of the more recent methods include signal processing capability to enhance the signal, to identify the effects of respiration, and to eliminate defective signals so that errors are not introduced into the final calculations. The techniques currently used for signal processing sometimes require electrocardiogram (ECG) measurements in addition to bioimpedance measurements and therefore increase the complexity of the system. Effective signal processing is generally the key to insuring accuracy in bioimpedance cardiography and improvements in this area can represent significant advances in the art.

SUMMARY OF THE INVENTION

The invention discloses a method of performing bioimpedance cardiography which allows medical practitioners to obtain an accurate, continuous assessment of a patient's cardiac performance.

The invention uses a series of spot electrodes placed on the surface of the patient's skin to generate a high frequency, low amplitude electrical current through the thorax of the patient and to measure changes in the generated current. The disclosed electrode configuration takes advantage of the physiological arrangement of electrical potential power lines in the body. As a result, the bioimpedance signal correlates closely with the desired cardiac parameters.

The invention also continuously adjusts the calculation of cardiac parameters according to changes in the red blood cell count and according to varying bodily compositions of different patients, and can thus be used under a variety of different circumstances without a loss of accuracy.

In addition, the invention discloses a system of improved bioimpedance signal processing. It employs a computer system to analyze the bioimpedance signal in a variety of ways to provide an accurate report of cardiac parameters. The computer system communicates a sinusoidal test curve to the transducer receiver and then measures and records the gain-phase-frequency distortions created by the receiver. The "real" bioimpedance signals subsequently received by the computer system through that transducer pass through filters which remove the transducer's characteristic distortions and other artifact. Accuracy of gain-frequency response and phase-frequency response is corrected to within 5%.

The invention derives and saves in memory a time-derivative bioimpedance signal. The curve generated by the time-derivative bioimpedance signal is plotted with respect to time and represents repeated cardiocycles. It is subject to very detailed analysis by the computer system. The power spectrum of the bioimpedance signal is calculated with discrete Fourier transforms and studied to estimate the patient's heart rate and to identify the fronts of each cardiocycle. A novel mathematical autoconvolution procedure is used to emphasize the heart rate harmonic in the time-derivative bioimpedance signal.

The invention removes breath waves by generating an envelope within the power spectrum in which cardiocycle signals should be found and then removing those signals which lie outside the envelope. The computer system also calculates the means and variances of peak-to-peak amplitudes for selected regions to further remove signals not indicative of a patient's cardiocycles.

The computer system employs a new method of deriving the effective left ventricular ejection time (ELVET) from bioimpedance signals. The derivation of ELVET is a detailed, multi-step analysis which involves finding various points on the time-derivative bioimpedance curve and determining which of these points most accurately reflect cardiac events. It requires making a variety of mathematical calculations, including making approximations for differentials of the time-derivative bioimpedance curve.

After the computer system calculates ELVET, it employs an improved form of Kubicek's equation to derive Heart Stroke Volume from ELVET, blood resistivity, the patient's specific body constitution, and the maximum bioimpedance change. It then analyzes the time-derivative bioimpedance signal further to eliminate cardiocycles with certain aberrations and recalculates the desired cardiac parameters.

BRIEF DESCRIPTION OF THE DRAWINGS

FIG. 3 depicts anatomical zones of interest for placement of measuring chest electrodes according to the present invention;

DETAILED DESCRIPTION OF THE PREFERRED EMBODIMENT

The first step in the present invention involves taking bioimpedance measurements over segments of tissue on a patient's body. Electrodes must be placed at appropriate points on the surface of the skin to generate a high frequency, low amplitude electric current and to detect changes in the generated current after it passes through the segments of tissue (see FIGS. 2A, 2B, 3 and 4). The electrodes are "spot electrodes" rather than "band electrodes" in order to maximize the free area on the patient's body. The spot electrodes are preferably of the disposable, one-use type. The patient thus has increased freedom of movement and medical practitioners have more access to the patient's skin for other medical procedures, such as the introduction of catheters and the administration of anesthesia.

The electrode system employs a total of six electrodes: a pair of detecting (measuring) electrodes at the appendix level, a pair of detecting (measuring) electrodes positioned laterally on the neck, an influencing electrode on the left leg, and an influencing electrode on the forehead.

The influencing electrodes may be standard ECG spot electrodes with a contact area of 2×2 cm. The upper influencing electrode is preferably placed on the middle of the forehead, at the mid-line thereof. The lower influencing electrode is preferably placed on the left knee or somewhere below the left knee such as the left foot. If necessary, the lower influencing electrode may also be placed above the knee level, provided that the following condition is satisfied:

$L > 5R$, where L is the distance between influencing electrodes and R is the radius of the chest. The left leg is used instead of the right leg to account for the anatomic asymmetry of the heart. The physiological positioning of the aortic arch, through which a significant concentration of electrical potential power lines pass, makes the left leg most suitable for the lower influencing electrode. The arrangement of influencing electrodes in this manner guarantees the uniform distribution of influencing current power lines between measuring electrodes and thus helps to minimize the error in the final cardiac parameter measurements.

The upper pair of measuring electrodes may also be standard ECG spot electrodes with a contact area of 2×2 cm. These electrodes are placed symmetrically along the lateral lines of the patient's neck, approximately 4 cm above the base of the neck. The base of the neck is defined to be located at the point of maximum curvature of the lateral lines of the neck. Placing the upper measuring electrodes in this area avoids the error that would otherwise result from the nonlinearity of electrical power lines at the neck-chest junction.

The lower chest pair of measuring electrodes each have a contact area of 12 to 30 $cm_2$. If this contact area is either reduced or enlarged, the heart stroke volume will be underestimated. A contact area of less than 12 $cm^2$ provides insufficient depth of measurement, a particularly serious problem with larger patients, and a contact area of more than 30 $cm^2$ causes the measurement to extend into additional anatomical regions.

Figure 2A:
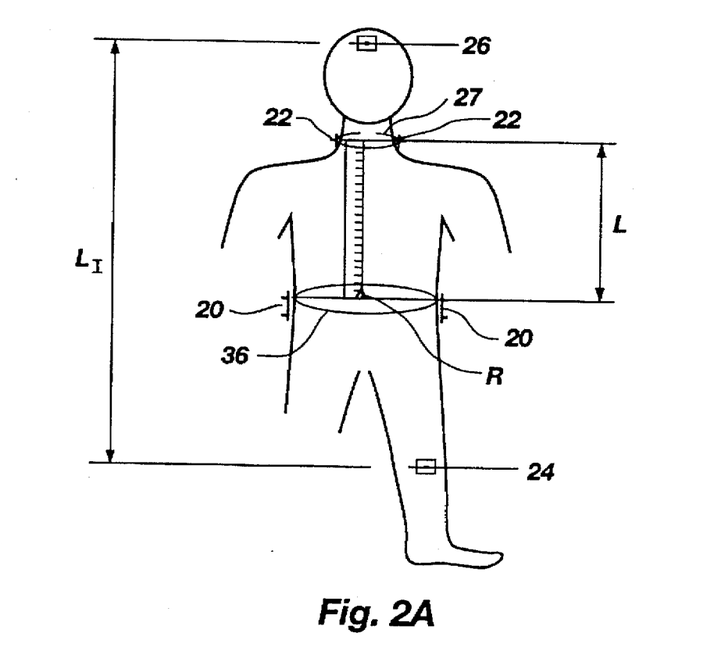
FIGS. 2A, 2B and 2C schematically depict spot-type electrode placements according to the present invention.
Figures 2B, 2C, 3A, 3B:
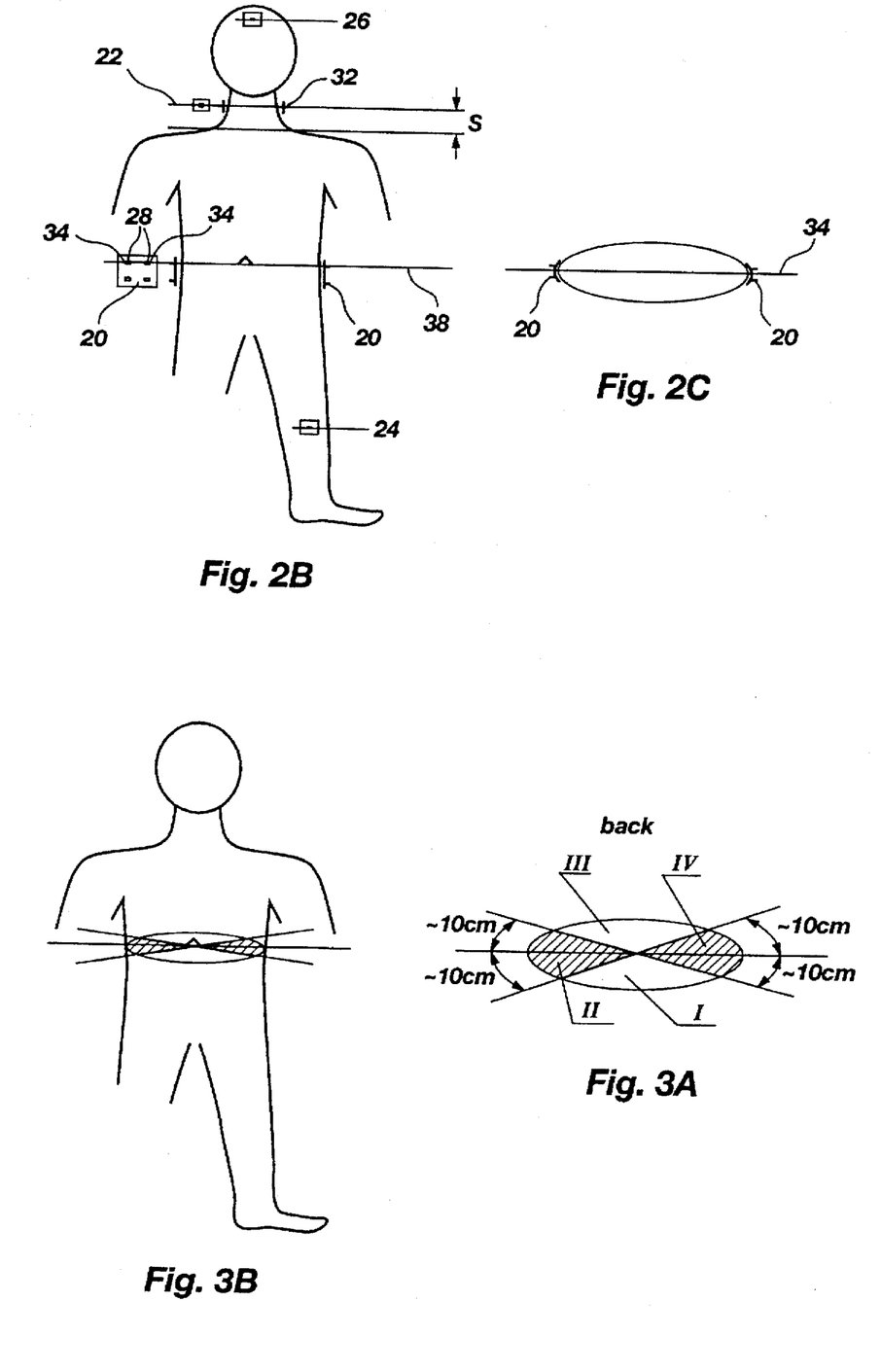
Figure 4:
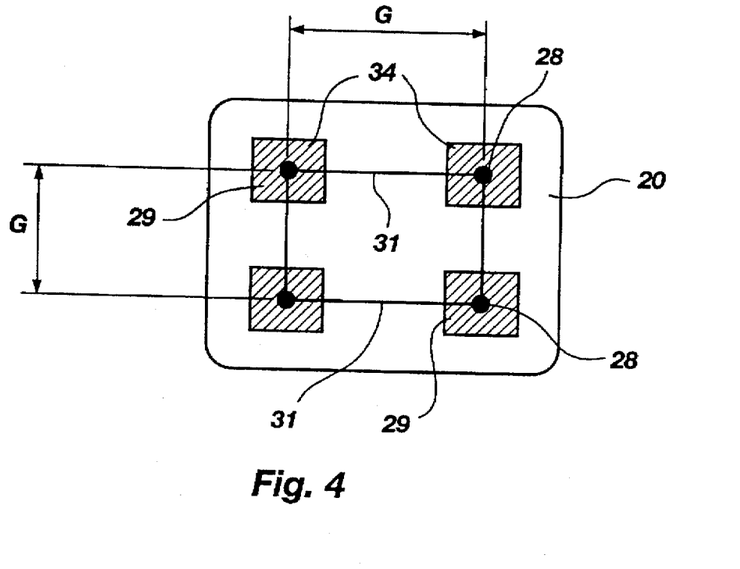
FIG. 4 illustrates the structure of an individual chest electrode according to the present invention.

The individual chest electrodes are each preferably comprised of a set of four standard ECG spot electrodes, each with a contact area of 2×2 cm with the top pair of spot electrodes of each chest electrode at appendix level (see FIGS. 2B and 4). Such a design takes advantage of the anatomic features of zones I and III of the body (see FIG. 3) and insures a minimum of error since the measurement is taken at an adequate depth and allows for variations in the bodily constitutions of different patients. The chest electrodes as described are placed laterally on opposite sides of the chest (see FIGS. 2A and 2B).

The influencing electrodes generate a high frequency, low amplitude current into the patient's body and the detecting electrodes measure the current after it passes through body tissue. The electrical impedance of the tissue can readily be determined from the difference between the generated current and the measured current. The electrical impedance of the tissue varies over time as a result of blood flow, respiration, and other factors.

A computer system, which may comprise a specifically programmed general purpose computer such as a personal computer, receives the electrical current measurements from the detecting electrodes, determines the bioimpedance of the interceding tissue as a function of time, and ultimately calculates HR (heart rate), SV (heart stroke volume), and CO (Cardiac Output). The bioimpedance signal is labeled as Z(x) and the bioimpedance signal differentiated with respect to time is labeled Y(x). The equation for determining SV is given as follows:

$$SV = K \cdot P \cdot ELVET \cdot (L/Z_0)^2 \cdot (dZ/dt)_{max}$$

where K is a novel scale factor, P is the specific blood resistivity, L is the distance between the inner voltage sensing electrodes, $Z_0$ is the mean or base thoracic impedance (determined from the inner electrodes), ELVET is the effective left ventricular ejection time, and $(dZ/dt)_{max}$ is the maximum negative slope change of the time-differentiated impedance signal obtained from the two inner electrodes.

The K term accounts for variations in body compositions of different patients. In order to obtain a value for K, the medical practitioner first measures the height and weight of the patient and the perimeter of the patient's neck and chest using conventional means or commercially available ultrasonic measuring means. The medical practitioner then inputs these values into the computer system, which in turn uses the values to compute the effective cross-sectional area of the chest and the total surface area of the body. The effective cross-sectional area of the chest is given by:

$$SCHEST = (PCHEST^2 + PNECK \cdot PCHEST + PNECK^2)/12\pi,$$

where PCHEST is the perimeter of the patient's chest and PNECK is the perimeter of the patient's neck. Then K is calculated as follows:

$$K = K_0 - K_1 \cdot (SCHEST/(H^{K_2} \cdot W^{K_3})),$$

where H is the patient's height, W is the patient's weight, and $K_0$, $K_1$, $K_2$, $K_3$ are gender and age dependent and lie in ranges:

$$K_0 \in [1-4]; \ K_1 \in [3-16]; \ K_2 \in [0-1]; \ K_3 \in [0.1-2]$$

The present invention can thus be used on patients of varying body constitutions without a loss of accuracy.

The electrical resistivity of human blood is not a constant. It varies among different individuals and even in the same individual at different times. Blood resistivity is particularly susceptible to fluctuation in patients undergoing blood infusion. As a result, an accurate system of bioimpedance cardiography must include means for continuously modifying the blood resistivity term of the Kubicek equation.

A patient's specific blood resistivity depends largely upon his or her hematocrit. The relationship between these two values for capillary blood is as follows:

$$P = 13.5 + 4.29 \cdot H,$$

where P is the specific blood resistivity and H is the capillary hematocrit. This relationship is adopted from V.I. Arinchin et al., "Taking into account electrical resistance of blood will increase accuracy of chest tetrapolar rheography method," Journal of Pediatrics (U.S.S.R.) 1987, v. 7, pp.59–52. The hematocrit can be measured using any commercially available method. It may either be inputted into the computer system by the medical technician, or sent by electronic means directly from the hematocrit measuring device.

The invention utilizes a novel method for processing the bioimpedance signal comprised of the following steps:

(i) digital filtration and phase correction, (ii) heart rate estimation, (iii) suppression of breath waves, (iv) determination of cardiocycles, (v) arrangement of check points, and (vi) selection of cycles without interference artifacts.

Figure 8A:
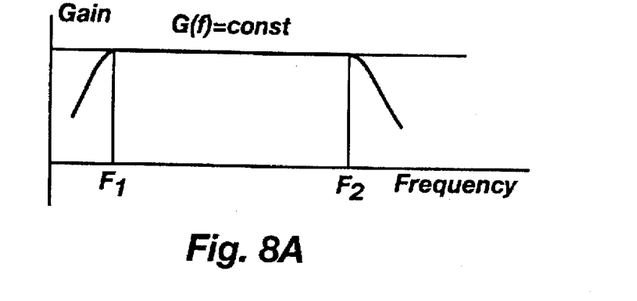
FIG. 8 depicts the resulting GPF characteristics of a transducer signal as corrected by an R-filter according to the present invention.
Figure 8B:
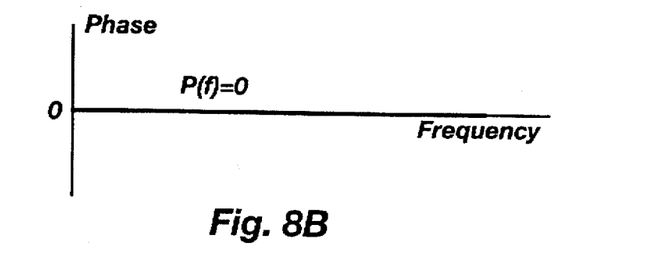

The first pan of the electronic filtration involves passing the signal through a "restoring" R-filter to achieve gain-phase-frequency (GPF) correction. The R-filter compensates for the distortions caused by the particular electronic transducer that is used to measure bioimpedance changes. It is well known that GPF characteristics of a bioimpedance transducer (FIG. 7) may greatly influence the shape of the bioimpedance curve. These interferences must be removed from the signal. The R-filter uses posterior signal processing to correct linear GPF distortions. It is constructed in such a way that the system of the bioimpedance transducer plus R-filter has GPF characteristics with zero phase shift and constant gain at the given range of frequencies, for example from 0.3 to 30 Hz for the bioimpedance signal (see FIG. 8). Thus, correlation of the outputs of different bioimpedance devices may be achieved. With the exception of the filter parameters and operating characteristics specified as desirable or critical for the R-filter and other filters described herein, construction of same is conventional and within the ability of those skilled in the art, and so will not be further described.

The first step of the GPF correction involves connecting the bioimpedance transducer with a source of an electrically-generated sinusoidal impedance signal and then measuring the output from the transducer. The electronically-generated sinusoidal impedance signal has an amplitude of 0.1 Ohm with respect to a baseline, for example, 375 Ohm. Such a signal has been developed using a voltage-to-impedance converter consisting of a photoresistor, a photoemitter (photo diode), a power supply, and an analog-digital-analog (ADA) computer interface. The paired photoresistor and photoemitter are coupled inside a light-protected housing so that the photoresistor changes its impedance according to the photoemitter's light intensity. The ADA conversion process includes digital-to-analog conversion of the mathematically-modeled sinusoid with a frequency of 19 kHz and analog-to-digital conversion with a frequency of 100 Hz, with 12 bit resolution. Through the interface, the computer produces a set of test sinusoidal signals with frequencies in the range from 0 to 75 Hz and records the responses of the transducer. The operating characteristics of the voltage-to-impedance converter include an input signal of 0 to 5 V, an output signal of −0.1 to 0.1 Ohm with a baseline of 375 Ohm (as previously noted). The GPF characteristic H(f) of the transducer may be calculated then from the spectrums of the initial test signals and the resulting responses of the transducer and presented as a graph or stored in an ASCII or other memory file. The system uses the calculated GPF characteristic H(f) of the transducer to calculate the "restoring" R-filter. The GPF characteristic of such R-filter can be formally written as 1/H(f) in a certain frequency range. The R-filter also provides frequency bounds through low and high frequency filters to provide suppression of random low and high frequency interference (see FIG. 7). The filtration with the R-filter may be done in the frequency domain using a Fourier transform. It is preferable to use a Gaussian window with Fourier transform to eliminate the boundary effects of the recorded signal:

$$G(t)=\exp(-2\cdot(\alpha\cdot t/(2\cdot T))^\wedge 2)$$

where $2\cdot T$ is a duration of recorded signal, $t<T$ is a time, and "a" is a predefined constant preferably in the range of 2.5–3. Multiplication of the Fourier image of the recorded signal by the R-filter's GPF characteristics results in suppression of GPF distortions and additional filtration of the signal. Reverse Fourier transformation and division by the Gaussian window may also be employed. The same steps may be employed in the time domain without Fourier transformation.

Figure 5A:
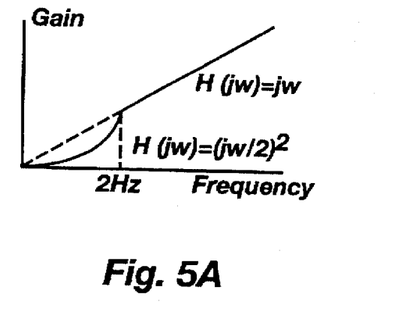
FIG. 5A is a graph of the gain versus frequency characteristics of an A-filter according to the invention employed for signal differentiations and harmonics suppression.
Figure 5B:
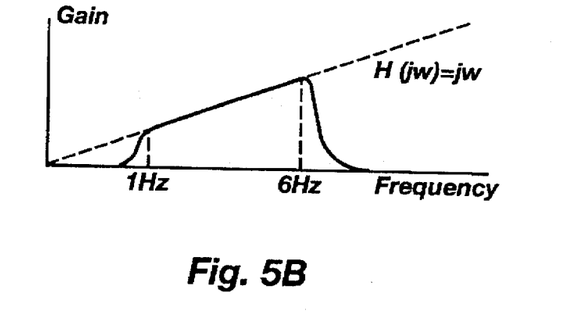
FIG. 5B is a graph of the gain versus frequency response of a B-filter as employed in the present invention to highlight the fronts of cardiocycles.
Figure 5C:
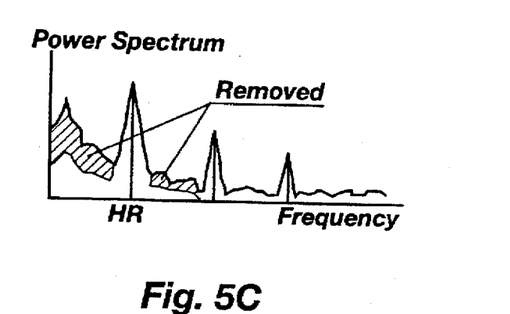
FIG. 5C is a graph of filtration employed to remove breath waves' power spectrum from the summary (breath and cardiowave) power spectrum in the present invention.

The signal after R-filtration is referred to as the "restored" signal, and this signal is used for further calculations. The next step in the bioimpedance signal processing is heart rate estimation. The power spectrum of the "restored" bioimpedance signal is then calculated with discrete Fourier transform and used to estimate the patient's heart rate (HR). Very often a breath harmonic is the highest one in the power spectrum of the bioimpedance signal. Consequently,it must be suppressed and the HR frequency response highlighted. A special transformation is used for this purpose. First, the power spectrum (PS) of the "restored" signal is multiplied with the gain-frequency characteristic of the A-filter (see FIG. 5A). This filter differentiates the signal and additionally suppresses harmonics below a certain frequency preferably selected at a range from 1 to 3 Hz because breath wave harmonics commonly lie below 2 Hz and HR harmonics above 0.8 Hz. The power spectrum of clear cardiosignal consists of repeated peaks at frequencies HR, 2·HR, 3·HR, etc. Consequently, the following autoconvolution of the power spectrum will emphasize the heart rate harmonic:

$$AS1(f)=PS\alpha(f)\cdot PSA(2f)\cdot PSA(3f)$$

where AS1(i) is a result of the autoconvolution of the power spectrum and PSa(i) is the power of a given spectral line with frequency i which previously passed though the A-filter. It is preferable to have in the above product only the first three elements PSa, because the higher the frequency is, the lower the signal-to-noise ratio. The computer system uses the autoconvolution to search for Mas, the maximum value of AS1(i) in the range of 0.6 to 5 Hz. The frequency associated with Mas is regarded as an estimation of HR. The estimation of HR is then used in additional filtration (see FIG. 5C) and cardiocycle-identification procedures.

The aberrations in the bioimpedance signal caused by respiration must be removed to increase accuracy and to insure proper identification of the cardiocycles. Usually, breath frequency is less than heart rate frequency, but breath waves create a power spectrum which overlaps the lowest harmonics of the power spectrum created by the cardiocycles. So, it is impossible to remove the breath waves' power spectrum from the summary power spectrum entirely (see FIG. 5C). Cardiac strokes are a more stable, repetitive process in comparison with breath. Consequently, we can consider that their power spectrum consists of several narrow peaks. All power spectrum harmonics between main cardiowaves' spectrum lines are combination of lateral slopes of these main spectrum lines and a noise power spectrum. If these internal harmonics are decreased, noise is mainly suppressed, and cardiowaves only slightly. As subsequently noted, these ideas form the basis for the algorithm for breath wave filtration. After estimation of the heart rate (HR), as described above, the first and second harmonics of the cardiowaves' spectrum are determined. The local minimums at the power spectrum nearest to these spectrum peaks can be considered as their bounds. All harmonics below the lower bound of the second peak except for those within the first peak bounds are multiplied by a predetermined value less than 1 (as schematically shown in FIG. 5C). This results in elimination of breath wave amplitude, because the latter's power spectrum lies in the multiplied zone, but only slightly affects the cardiowaves.

The next step in bioimpedance signal processing is cardiocycle detection. To highlight the fronts of the cardiocycles, the "restored" signal as mentioned above is passed through the B-filter (FIG. 5B). This is a differentiating filter with sinusoid-like frequency bounds. The pass band of the B-filter is adapted for frequency harmonics that produce a main contribution to cardiocycle front (preferably from 1 to 6 Hz). the area between a local minimum and the next local maximum at the signal passed through the B-filter is regarded as a cycle front and described with a peak-to-peak change in time and a peak-to-peak change in amplitude. The computer system then generates a time-amplitude envelope by analyzing the first five (5) harmonics of the power spectrum generated by the signal after it passes through the B-filter. The cycle fronts are examined and certain ones are marked for further analysis if their peak-to-peak changes in time and peak-to-peak changes in amplitude are within the time-amplitude envelope. To increase the reliability of cardiocycles recognition, the computer system calculates mean and variance of peak-to-peak amplitudes for the selected regions.

If the variance-per-mean ratio is less than a predetermined value, preferably 0.3, then all of the marked fronts are transmitted to the next stage which involves the arrangement of check points and the selection of defectless cardiocycles. In the alternative, if the variance-per-mean ratio is greater than a predetermined value, then additional analysis must be performed. The additional analysis comprises the following steps: (i) the regions under examination are separated into two groups according to their peak-to-peak amplitude: those above the mean value ("the upper group") and those below the mean value ("the lower group"); (ii) the means, M1 and M2, and variances, V1 and V2, are calculated for each group; (iii) the appropriate values are inserted into the following inequality for each group:

$$M2+\alpha \cdot V2 < M1-\alpha \cdot V1,$$

where a is a predetermined value, preferably 1.96, and V1 and V2 are standard deviations for the lower and upper groups respectively; and (iv) if the inequality holds true, then the regions in the upper group are taken to be the fronts of the cardiocycles and the regions in the lower group are eliminated from further consideration, otherwise all selected regions proceed to the next stage.

The computer system identifies certain check points in the time-differentiated bioimpedance signal to calculate the effective left ventricular ejection time, FJ-VET, as a preliminary step in determining heart stroke volume (SV).

The present invention uses ELVET, a term which represents only the left ventricular ejection time, rather than Kubicek's VET, a term which represents the combined left and right ventricular ejection times. It is known that the value of the time-differentiated impedance signal is proportional to peak aortic blood flow ejected by the left ventricle. Therefore, the most accurate calculation of SV requires that LVET be used. LVET is calculated from the following equation:

$$LVET = ELVET + LVPT,$$

where ELVET is the time between the moment the left ventricular valve opens and the moment that it begins to close, and LVPT is the protodiastoly time (the time it takes for the left ventricular valve to close). LVPT is not readily detectable with hemodynamic monitoring means because the changes in blood flow are insignificant during the protodiastoly time. For this reason, the present invention uses the product of ELVET and $(dZ/dt)_{max}$, the maximum absolute value of the first chest impedance derivative with respect to time, to account for the lack of an LVPT measurement.

Figure 9:
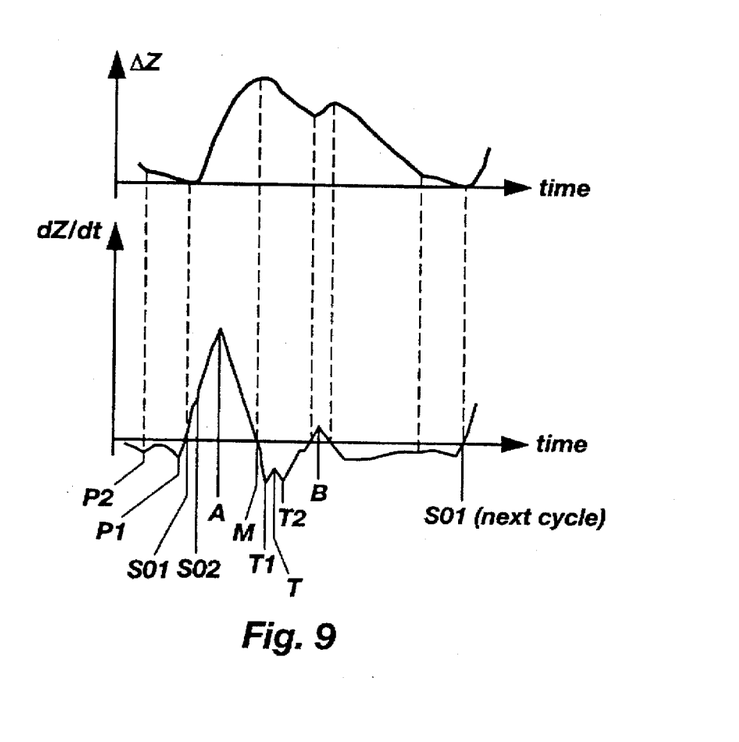
FIG. 9 is an illustration of a time-derivative bioimpedance signal generated according to the present invention, plotted with respect to time.

The calculation of ELVET requires an analysis of the curve generated by the graph of Y(x), the time-derivative bioimpedance signal, plotted with respect to time (see FIG. 9). The computer system first finds a global maximum of Y(x) over a given cardiocycle and designates it as point A. The beginning of ELVET is point $S_0$ and is taken to be either the point of x-axis crossing, point $S_{01}$, or the point of maximum curvature before point A, point $S_{02}$. The curvature of the bioimpedance signal is given as:

$$C(x)=Y''(x)/[(1+Y'(x)^2)^{3/2}],$$

where Y' (x) and Y" (x) are respectively the first and second derivatives of the time-differentiated bioimpedance signal, Y(k), with respect to time. The derivatives are estimated as follows:

$$Y'(k)=[Y(k+1)-Y(k-1)]/2$$

and $$Y''(k)=Y(k-1)-2 \cdot Y(k)+Y(k+1).$$

In order to identify the beginning of ELVET, point $S_0$, the computer system selects, after analysis of the first quarter of cardiocycle, either the algorithm for determining the x-axis crossing or the algorithm for determining maximum curvature. The algorithm for the x-axis crossing is preferable, but occasionally cannot be used because the time-differentiated bioimpedance signal curve crosses the x-axis before the beginning of ELVET. Such a premature crossing occurs most frequently with patients who have a rapid heart rate and low vascular system resistance. After $S_0$ is identified by the appropriate algorithm, an "effective" time for the start of ELVET, S", is calculated according to the following equation:

$$S''=A-[(Z(A)-Z(S_0))/(Y(A)/2)],$$

where A is the time associated with point A; Z(A) is the amplitude of the bioimpedance signal at point A; $Z(S_0)$ is the amplitude of the bioimpedance signal at point $S_0$; and Y(A) is the derivative of the bioimpedance signal at point A. If the asynchronism of the opening of the right and left valves is small, then S" coincides with $S_0$.

To identify the end of ELVET, the computer system first finds point $T_0$, which is taken to be either the first or the second local minimum after point A at the time differentiated bioimpedance signal, labeled as $T_1$ and $T_2$ respectively. The computer system chooses between $T_1$ and $T_2$ after an analysis of the depth of the curve at each point. If depth of the second minimum is greater than a predetermined fractional value of the depth of the first minimum, then $T_2$ is selected as $T_0$. Otherwise, $T_1$ is used. The "effective end" of the ventricular ejection, point T, is then identified as the nearest local minimum before point $T_0$ on the graph of the curve generated by the second derivative of the Y(x). ELVET is calculated as the time distance between points S" and T.

The inventive method of determining ELVET has been correlated to an ultrasound ELVET determination with a correlation coefficient of r=0.86. Kubicek's algorithm gives only a correlation of r=0.73. Consequently, and in contrast to Kubicek, left ventricular ejection time as measured by the inventive method is measured in substantial isolation from the right ventricular ejection time.

After the computer system arranges all check points, it eliminates cardiocycles with certain aberrations. Fuzzy logic and fitness algorithms may be employed in this procedure. Several criteria are used for this purpose. The computer system first confirms that the time distances between the points described above for each cardiocycle (e.g., point A, point T, Point S) do not exceed certain bounds. It also verifies that the amplitude difference between the start and the end of the cardiocycle do not exceed a predefined value. The amplitude change between the start and end of the cardiocycle must not exceed a predefined percentage of the maximum amplitude over that cardiocycle. Furthermore, the ratio of the time-derivative bioimpedance signal at point A to the time-derivative bioimpedance signal at point T must be greater than a predetermined value; that is:

$$Y(A)/Y(T)>c,$$

where Y(A) and Y(T) are the values of the time-derivative bioimpedance signal at points A and T respectively, and c is the predetermined value. The computer system then checks for the "neighbors criterion" to eliminate the effect of random noise in the bioimpedance signal. A three-dimensional "nearness" vector with elements (A1i, A2i, A3i) is calculated for each pair of cardiocycles. The individual elements of the nearness vector are determined using the following equations:

$$A1i=[Y(Ai)-Y(Aj)]/Y(Ai),$$

$$A2i=(Sti-Stj)/Sti,$$

and $$A3i=[[Y(Bi)-Y(Ti)]-[Y(Bj)-Y(Tj)]]/[Y(Bi)-Y(Ti)],$$

where Y(x) is the time-differentiated bioimpedance signal; A, T, and B are check point positions in each cardiocycle (see FIG. 9); ST is the time distance between points S and T; and i and j are different cardiocycles. The computer system compares all of the calculated nearness vectors and eliminates those cardiocycles wherein the amplitudes of the nearness vectors are not similar. The comparison is made using a two-threshold analysis. If the difference between the nearness vector amplitude of two cardiocycles is less than a first predefined value, L1, the similarity is considered "good." If the difference is greater than L1, but less than a second predefined value, L2, the similarity is considered "worse" or "marginal." Otherwise, the similarity is considered "bad." Cardiocycles with "good" amplitude similarity are used in the final calculations of hemodynamic parameters. Cardiocycles with "worse" or "marginal" amplitude similarity are only used in the final calculations if there are not enough "good" cycles. Cardiocycles with "bad" similarity are not used in the final calculations.

After the bioimpedance signal processing is complete, the computer system performs the final calculation of hemodynamic parameters, together with means and variances for the entire data block. Heart Rate (HR) and Heart Stroke Volume (SV) are recalculated using the respective methods described above, except that the processed bioimpedance signal is used instead of the unprocessed bioimpedance signal. Cardiac Output (CO) is calculated as the product of HR and SV; that is:

$$CO=SV \cdot HR.$$

Figure 6:
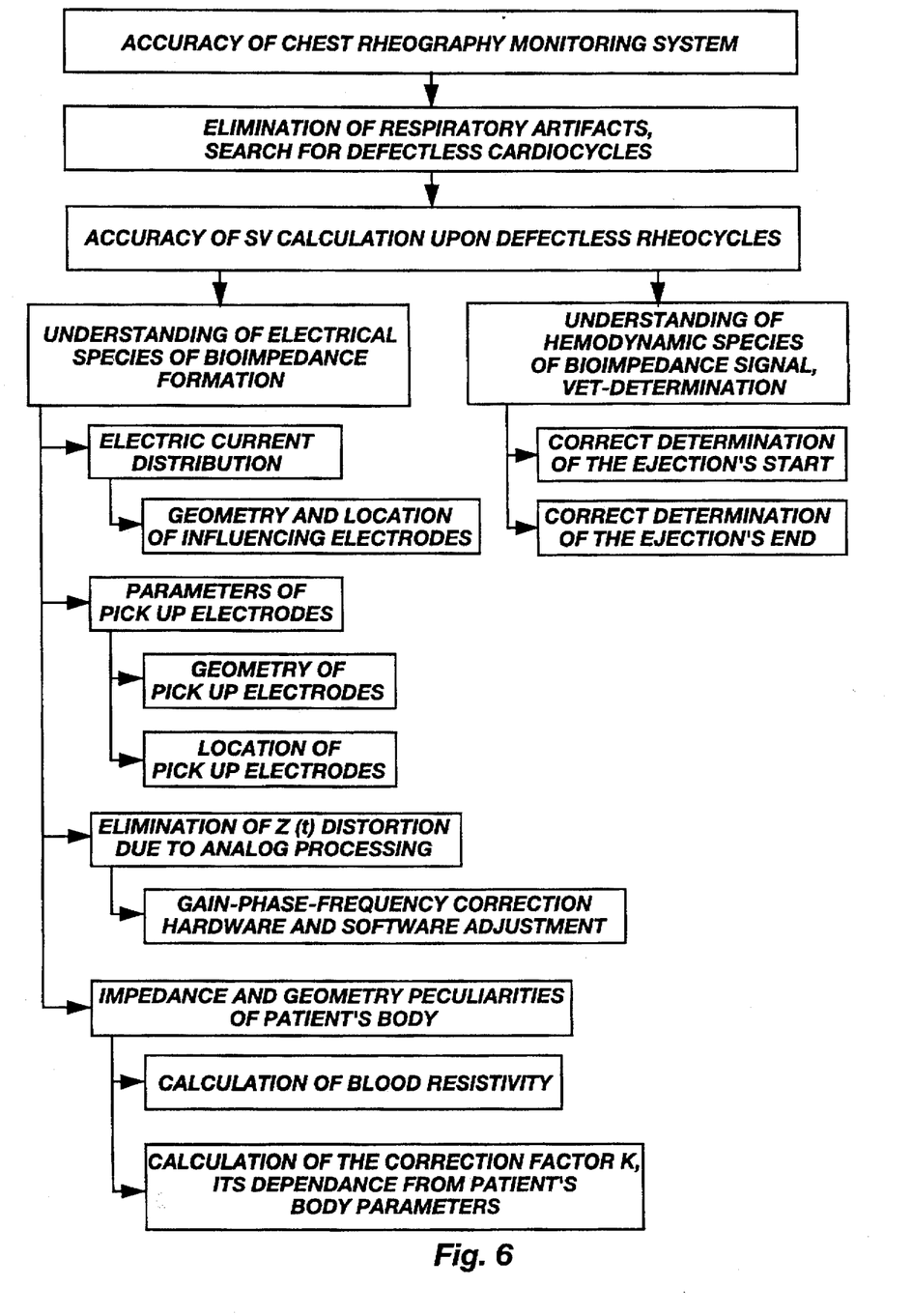
FIG. 6 is a flow chart of the methodology of the present invention.
Figure 7A:
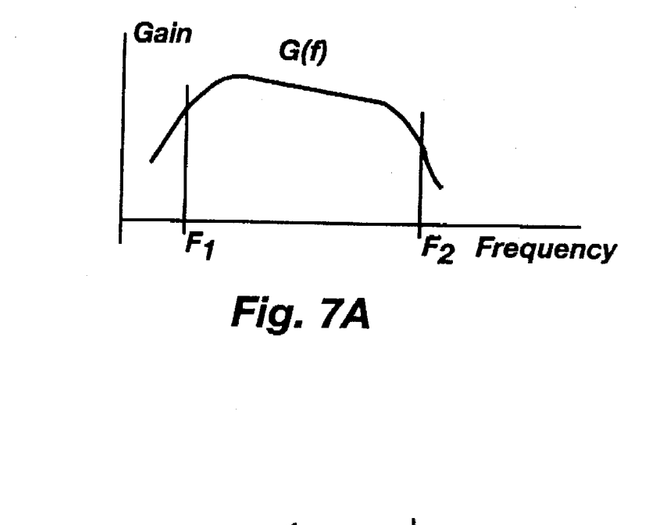
FIG. 7 depicts the GPF characteristics of a bioimpedance transducer according to the present invention and the corresponding characteristics of an "R" or restoring filter used for GPF corrections according to the present invention.
Figure 7B:
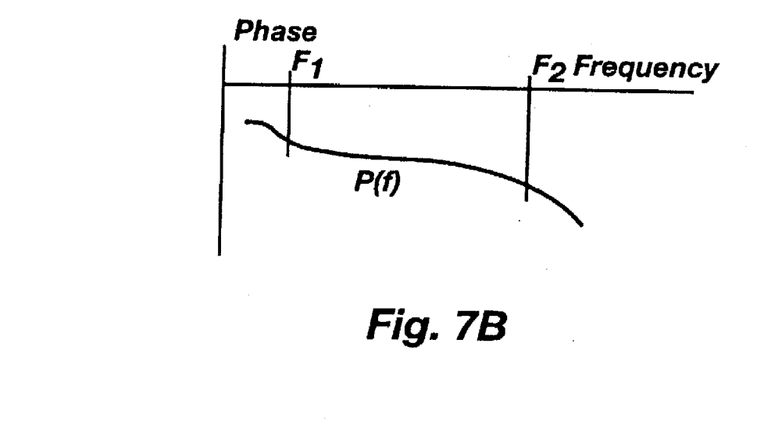
Figure 7C:
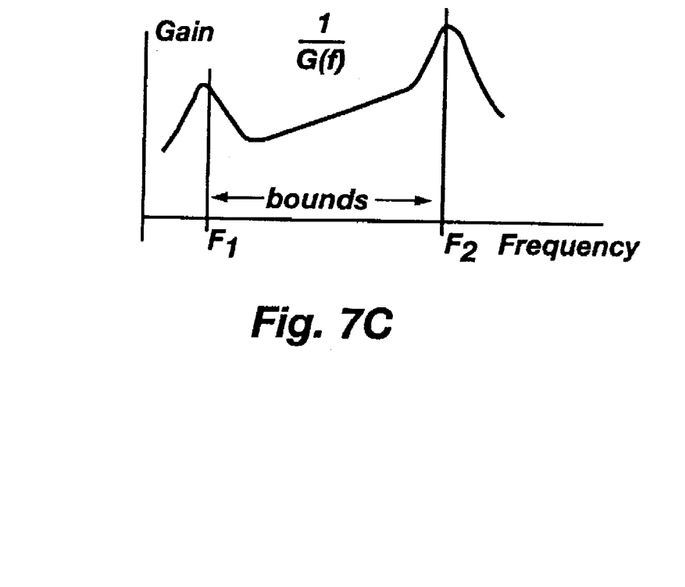
Figure 7D:
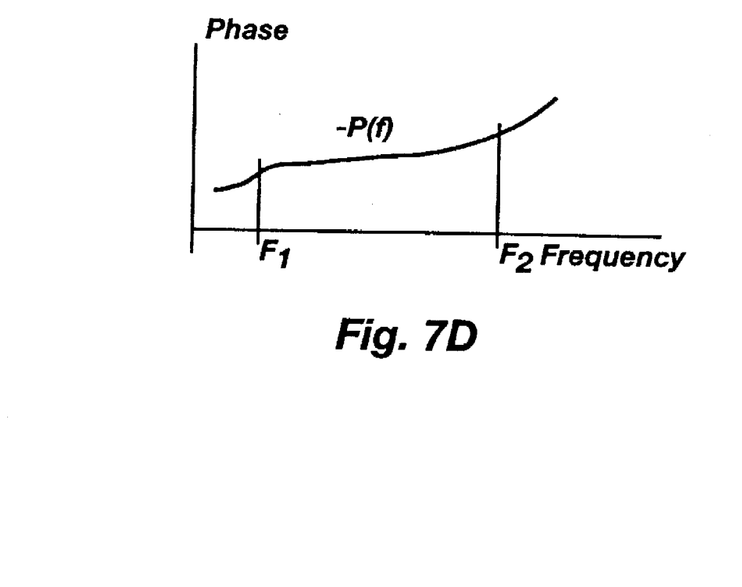

An outline of the methodology of the present invention is set forth in FIG. 6.

While the present invention has been described in terms of a preferred embodiment, those of ordinary skill in the art will recognize and appreciate that it is not so limited. Many additions, deletions and modifications to the disclosed embodiment may be made without departing from the scope of the invention as hereinafter claimed.

What is claimed is:

1. A method for processing a bioimpedance signal of a patient for derivation of heart rate, heart stroke volume, and cardiac output comprising:

digitally filtering and phase correcting the bioimpedance signal to remove gain-phase-frequency distortions;

estimating heart rate using a power spectrum of the bioimpedance signal, and an auto-convolution function of the said power spectrum;

suppressing breath waves to remove undesired power spectra components and generate a bioimpedance signal of restored shape;

determining cardiocycles of said restored bioimpedance signal;

determining effective left ventricular ejection time (ELVET) using check points within said cardiocycles; and discarding at least some of said cardiocycles which exhibit interference artifacts.

2. The method of claim 1, wherein determining the effective left ventricular ejection time (ELVET) further comprises:

locating points on a time-derivative bioimpedance curve for the bioimpedance signal; and selecting the points which most accurately reflect cardiac events.

3. The method of claim 1, further comprising determination of phase-frequency and gain-frequency characteristics of a transducer employed in detection of the bioimpedance signal prior to use thereof in said detection, and correcting for signal distortion in the output of said transducer attributable to said characteristics.

4. The method of claim 3, wherein said determination comprises:

generating a high precision sinusoidal impedance signal with peak-to-peak impedance of approximately 0.2 Ohms and baseline impedance of approximately 375 Ohms;

connecting said sinusoidal impedance signal to said transducer;

measuring the output from said transducer; and calculating gain-phase-frequency characteristic, H(f), of the transducer in a predefined frequency range.

5. The method of claim 4, further comprising generating said high precision sinusoidal impedance signal using a voltage-to-impedance converter including a photoresistor, a photoemitter, a power supply and an analog-to-digital-to analog computer interface.

6. The method of claim 5, further comprising producing through said interface a set of test signals with predefined amplitude and frequency range, detecting an output signal from said transducer, and analyzing said output signal to determine said phase-frequency and said gain-frequency characteristics.

7. The method of claim 3, further comprising employing posterior signal processing to correct linear gain-phase-frequency distortions by converting real operating characteristics of the transducer to predefined characteristics, wherein phase shift is zeroed and gain is assumed to be constant in a predefined frequency range.

8. The method of claim 1, wherein estimating heart rate further comprises:

calculating a power spectrum of the bioimpedance signal;

multiplying said power spectrum by a selected amplitude-frequency function to differentiate the signal and suppress breath harmonics;

autoconvoluting the resulting power spectrum according to the formula:

$$AS1(f)=PS\alpha(f) \cdot PS\alpha(2f) \cdot PS\alpha(3f);$$

and determining a maximum amplitude value of autoconvolution in a predefined frequency range as an estimation of heart rate.

9. The method of claim 1, wherein determining cardiocycles further comprises:

filtering the bioimpedance signal to emphasize fronts of cardiocycles;

calculating a time-amplitude envelope of said cardiocycles by analyzing the first five harmonics of the power spectrum of said bioimpedance signal after said filtration; selecting said cardiocycle fronts by comparison with said calculated time-amplitude envelope; and rejecting erroneously-detected fronts.

10. The method of claim 1, wherein discarding cardiocycles exhibiting interference artifacts further comprises:

detecting time and amplitude relations referencing check points within individuals of a plurality of cardiocycles;

comparing said time and amplitude relations between individuals of a said plurality of cardiocycles; and further examining selected cardiocycles which exhibit the presence of artifact according to a plurality of comparison criteria.

11. The method of claim 10, further comprising:

constructing a multi-dimensional vector for each selected cardiocycle;

comparing said multi-dimensional vector with such vectors for other cardiocycles; and rejecting the cardiocycles with vectors having no neighboring vectors of other cardiocycles.

12. The method of claim 1, wherein determining effective left ventricular ejection time (ELVET) comprises:

filtering the bioimpedance signal and suppressing breath waves therein;

detecting a cardiocycle;

calculating the time derivative of the bioimpedance signal;

determining the maximum value of the time derivative;

determining effective ejection start time;

determining effective ejection end time; and calculating effective left ventricular ejection time (ELVET) as change in time between effective ejection start time and end time.

13. The method of claim 1, further including determining stroke volume by:

determining specific blood resistivity P;

measuring a distance L between two bioimpedance electrodes applied to the patient;

determining the base thoracic impedance $Z_0$;

determining ELVET;

and calculating stroke volume SV according to the equation $$SV = K \cdot P \cdot ELVET \cdot (L/Z_0)^2 \cdot (dZ/dt)_{max}$$

where K is a novel scale factor related to body composition of the patient.

14. The method of claim 13, further comprising calculating K as:

$$K = K_0 - K_1 \cdot (SCHEST/(H^{K_2} \cdot W^{K_3})),$$

where:

$$SCHEST = (PCHEST^2 + PNECK \cdot PCHEST + PNECK^2)/12\pi.$$

15. The method of claim 4, wherein $K_0$, $K_1$, $K_2$, $K_3$ are gender and age dependent and lie in ranges of $$K_0 \in [1-4]; K_1 \in [3-16]; K_2 \in [0-1]; K_3 \in [0.1-2].$$

16. The method of claim 13, further including determining cardiac output as a product of stroke volume and heart rate.

17. The method of claim 1, wherein suppressing breath waves further comprises:

calculating the Fourier transform of the bioimpedance signal;

locating the first and second frequency harmonics of cardiocycles in the calculated spectrum of the signal;

estimating the width of each of the harmonics;

suppressing frequency harmonics below the lower bound of the second harmonic except for harmonics within the bounds of the first frequency harmonic; and calculating the inverted Fourier transform of the signal.

18. The method of claim 1, wherein an electrode array is employed for detecting said bioimpedance signals, and further comprising:

placing an upper influencing electrode on the patient's head;

placing a lower influencing electrode on the left lower extremity of the patient;

placing an upper pair of detecting electrodes on the patient's neck; and placing a lower pair of detecting electrodes on the trunk of the patient.

19. The method of claim 18, further comprising:

placing said upper influencing electrode on the patient's forehead;

placing said lower influencing electrode in the general area of the patient's left knee;

placing said pair of upper detecting electrodes on the patient's neck; and placing said pair of lower detecting electrodes laterally on opposite sides of the patient's chest.

20. The method of claim 19, wherein said upper influencing electrode comprises a spot electrode, and further comprising placing said upper influencing electrode substantially on an intersection of vertical and horizontal center lines of said patient's forehead.

21. The method of claim 19, wherein said lower influencing electrode comprises a spot electrode, and further comprising placing said lower influencing electrode at a location which satisfies the relationship L<5R, where L is the vertical distance between said upper and said lower influencing electrodes and R is the radius of said patient's chest.

22. The method of claim 19, wherein said upper detecting electrodes comprises a pair of spot electrodes and said placement thereof is oriented symmetrically on opposite sides of said patient's neck along a horizontal line approximately 4 centimeters above the base of said patient's neck.

23. The method of claim 19, wherein said lower detecting electrodes further comprise a pair of electrode assemblies, each assembly providing contact surface area between about 12 and about 30 square centimeters, and further comprising orienting said assemblies laterally on opposite sides of said patient's chest at approximately appendix level.

24. The method of claim 23, wherein each assembly further comprises four spot electrodes, wherein each spot electrode comprises approximately 4 square centimeters contact surface area with each said spot electrode centered at corners of a square with sides measuring 5 centimeters, and all 4 spot electrodes of said assembly electrically connected to each other.

25. The method of claim 24, further comprising placing the top spot electrodes of each assembly on the sword-shaped appendix level of the patient.

* * * * *